US005283969A

United States Patent [19]

Weiss

[11] Patent Number: 5,283,969

[45] Date of Patent: Feb. 8, 1994

[54] IDENTIFICATION BAND

[76] Inventor: Steven J. Weiss, 84 Village Cir., Bridgewater, N.J. 08807

[21] Appl. No.: 921,554

[22] Filed: Jul. 29, 1992

[51] Int. Cl.[5] ..................... A61B 5/103; A44C 5/00

[52] U.S. Cl. ..................... 40/633; 63/3; 446/26

[58] Field of Search ..................... 40/665, 633; 63/1.1, 63/2, 3; 446/26

[56] References Cited

U.S. PATENT DOCUMENTS

| | | | |
|---|---|---|---|
| 267,164 | 11/1882 | Di Moriano | 63/1.1 |
| 2,096,389 | 10/1937 | Bode | 63/1.1 |
| 2,462,425 | 2/1949 | Pratt | 63/3 |
| 2,641,074 | 6/1953 | Richmond | 63/3 |
| 3,279,107 | 10/1966 | Baumgartner | 40/633 |
| 3,467,246 | 9/1967 | Long et al. . | |
| 3,965,589 | 6/1976 | McDermott | 40/633 |
| 4,936,699 | 6/1990 | Yoshida | 446/26 |
| 5,023,956 | 6/1991 | Fox | 40/633 |

FOREIGN PATENT DOCUMENTS

| | | | |
|---|---|---|---|
| 8904706 | 6/1989 | European Pat. Off. | 446/26 |

OTHER PUBLICATIONS

Baxter Hospital Supply Division Catalog, pp. B2–B7.
Precision Dynamics Company Identification Band.
Mac Lee ® Identification Band.

*Primary Examiner*—Peter M. Cuomo
*Assistant Examiner*—Flemming Saether

[57] ABSTRACT

An identification band having a pocket portion and a strap portion extending from the pocket portion. The pocket portion encloses identification information pertaining to the wearer. The periphery of the pocket portion is configured to convey a creative artistic impression, that is, a configuration resembling at least a portion of any one of a living being (alive now or in the past), cartoon character, a man-made functional article (such a transportation vehicle and a building), a natural object (such as a cloud or star) and a decoration (such as holiday decorations and artwork). The pocket portion may be relatively planar or be formed so that the artistic impression is three-dimensional.

8 Claims, 1 Drawing Sheet

FIG. 1
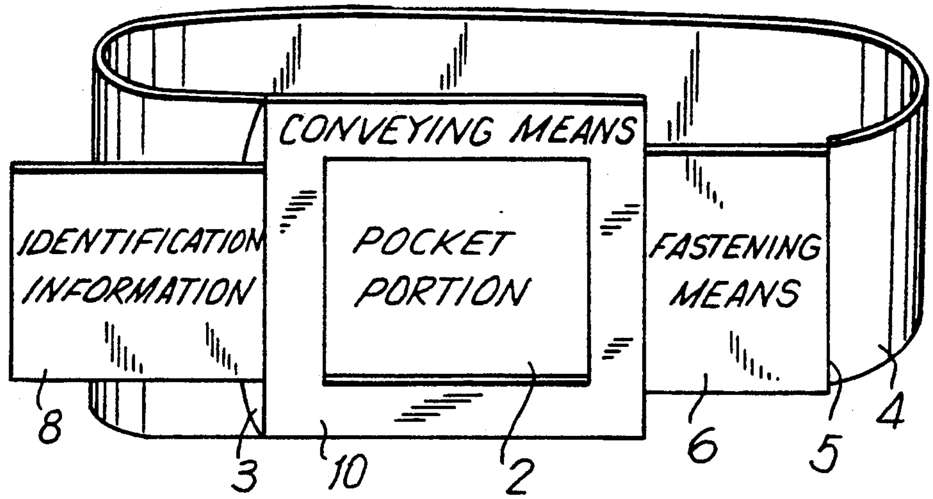
FIG. 2
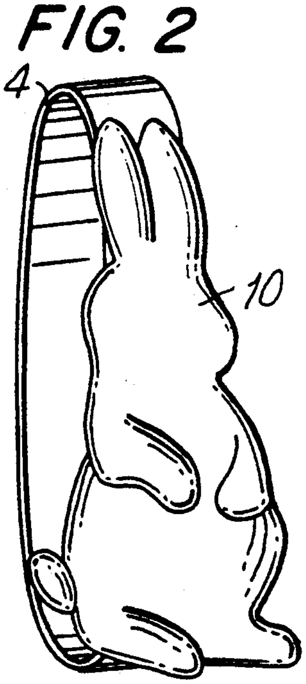
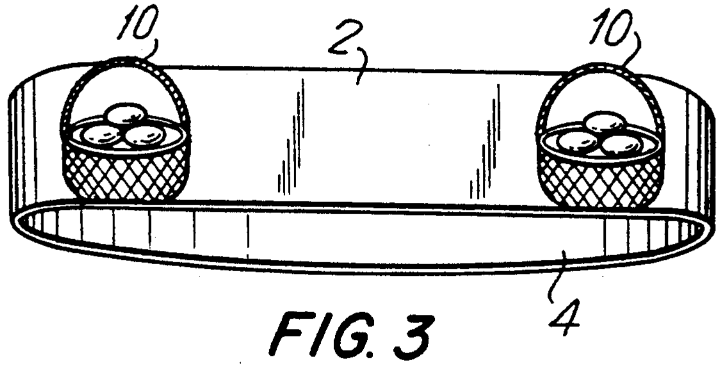
FIG. 3
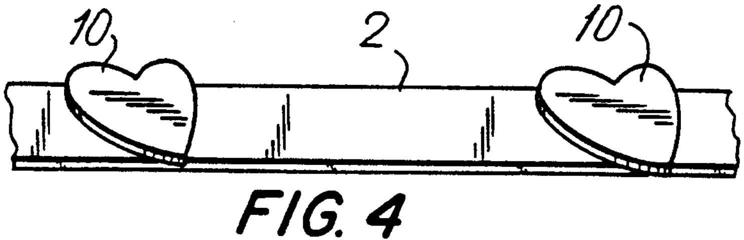
FIG. 4
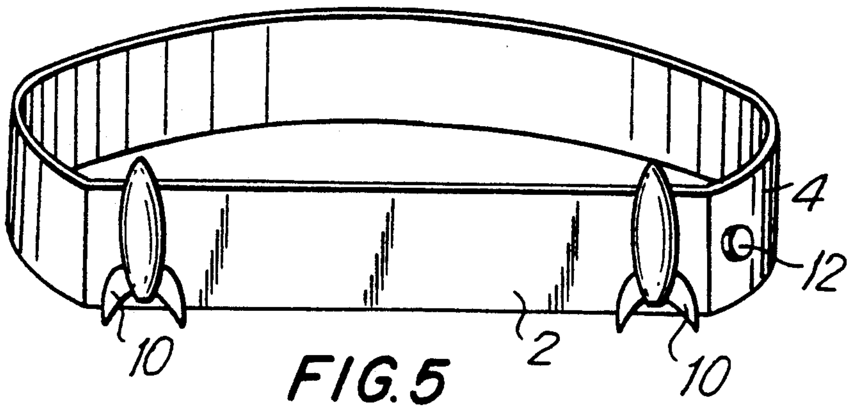
FIG. 5

IDENTIFICATION BAND

BACKGROUND OF THE INVENTION

1. Field of the Invention

The present invention relates to an identification band, suitable for use in hospitals and other medical facilities for identifying personal and/or medical information about the wearer.

2. Discussion of the Related Art

Identification bands are well known as exemplified by U.S. Pat. No. 3,467,246, whose contents are incorporated herein by reference.

Such prior art identification bands typically have an identification pocket portion, which encloses identification information about the wearer of a personal and/or medical nature. The band also has a strap portion which extends from one side of the pocket portion and may be secured at its free end to the opposite side of the pocket portion. The pocket portion is made from multiple plies with one of the face plies being transparent to allow viewing of the enclosed identification information. The periphery of the pocket portion is rectangular with rounded corners.

The wearer of the band may be a child, who must cope with the sterile, unfamiliar environment of the hospital or other medical facility. Often, all the child's personal and wearable belongings are taken away for the duration of the stay. The child wears hospital attire, including the identification band. Needless to say, the child may well feel uncomfortable, if not abandoned, while away from loved ones and familiar surroundings.

The prior art identification band, for which the pocket portion has a generally rectangular shape, is of limited appeal to the child, infant or adult because of its simple geometric shape. It would therefore be desirable to provide an identification band which was more appealing to children, infants and/or adults (e.g., the parents).

In addition, the identification band is often retained by parents of the child or infant as a keepsake. For instance, the band may take on a special significance to the parent if the stay was for child birth.

After the child is discharged, the parents may show off the identification band to family and friends or view it again when reviewing keepsakes of the child. If the identification band conveys the impression of a sterile, cold environment, it will be of little value in promoting the services of the hospital or medical facility in the future should the child again need medical treatment. On the other hand, an identification band which conveys the feeling of a warm, caring place may be of great service as promotion for return visits to the same facility.

SUMMARY OF THE INVENTION

The present invention is directed to an identification band having a pocket portion and a strap portion extending from the pocket portion. The band has a configuration on it which resembles that of at least a portion of any one of a person, animal, plant or thing, such as a cartoon character, functional manufactured article, natural object, or decoration. The configuration extends at least as far as the peripheral edge of and adjacent portion of the band element to provide enhanced visual effect and so that its contour may be touched by running one's finger along the peripheral edge of the band element.

The functional manufactured articles include transportation vehicles, buildings, monuments, appliances, toys and other articles which may be familiar to or recognized by children or adults as being "manufactured", which refers to products which are either formed (e.g., molded or cast) or assembled (e.g., either friction fit or fastened) or otherwise put together. The natural object includes a cloud, star, planet, rainbow, national landmark and other objects which may be familiar to or recognized by children or adults. The decoration includes artwork of a creative nature such as sculpture or artform associated with a holiday or special occasion; however, a single rectangle with curved corners is not creative and, therefore, does not fall under this category.

BRIEF DESCRIPTION OF THE DRAWINGS

For a better understanding of the present invention, reference is made to the following description and accompanying drawings, while the scope of the invention is set forth in the appended claims.

FIG. 1 is a perspective view of an identification band in accordance with the invention.

FIGS. 2–8 are each a perspective view of different embodiment of the identification band of FIG. 1 in accordance with the present invention.

FIGS. 9–26 are each a front view of a different embodiment of the identification band of FIG. 1 in accordance with the present invention.

FIGS. 27–28 are front and perspective views of still another embodiment of the identification band of FIG. 1.

FIGS. 29–30 are front views of further embodiments of the invention.

DESCRIPTION OF THE PREFERRED EMBODIMENT

FIG. 1 schematically represents an identification band having a pocket portion 2 with sleeve opening 3, a strap portion 4 with a free end 5, a fastening means 6 for fastening the free end 5 and the pocket portion 2 together in any known manner of fastening. The pocket portion 2 and the strap portion 4 together constitute a band element. Identification information (e.g. printed on paper) 8 may be inserted into the open sleeve 3, preferably in the same manner as disclosed in U.S. Pat. No. 3,467,246. The conveying means 10 is a configuration which resembles at least a portion of an outline of a person, animal, plant, man-made functional article, natural object, creative decoration, cartoon character or imaginary thing. The configuration conveys a creative artistic impression and may be either planar or three-dimensional. The more complex the familiar configuration, the more interesting to the wearer.

FIG. 2 shows an identification band having the pocket portion 2 and the strap portion 4, which extends away from one side of the pocket portion 2. The strap portion has a free end and is to be wrapped around the wrist of the wearer. The free end is fastened to the opposite side of the pocket portion in any known manner, such as in U.S. Pat. No. 3,467,246. The composition of the materials forming the identification band may be of any flexible material, preferably the same as that employed in U.S. Pat. No. 3,467,246.

FIG. 2 shows an artistic impression which is conveyed by a configuration in the form of an outline of a rabbit standing on hindlegs in a side position. Other examples of configurations include a rabbit in a front position standing on hind legs, a rabbit in a side position on all four legs, a bear, a duck, a song bird and a cat. These depictions are exemplary only; it is envisioned that the animals may be in any position and be of any type. The term "animal" is to be construed to mean any life form which is neither a person nor a plant and so would include, for example, fish and insects. Other configurations include a spaceshuttle, a jet and a truck and which are exemplary of transportation vehicles.

The intent of configurations is to represent something which is easily recognized or familiar to the child wearing the band. Thus, the configuration may be of a person, an animal, a flowering plant, a cartoon character, a functional manufactured article exemplified by a building (such as a house or skyscraper) or by a transportation vehicle (such as a jet, car, bicycle, ship, spacecraft, or truck) which a child might be expected to play with if made in miniature as a toy, a natural object (such as a rainbow, cloud, a star, a planet or national landmark), or a decoration of creative artwork (such as sculpture or an artform as may be associated with an occasion or event). The creative artwork would exclude a single rectangular shape having rounded corners because its simple geometric shape would not be creative. Multiple geometric shapes, however, are envisioned as an embodiment of the invention because the combination of such geometric shapes taken together form a pattern which is creative.

The configuration may be of only a portion of the person, animal, plant, article, decoration, cartoon character or object. For instance, the configuration may be of just an extremity of a person, e.g., the head or hand. It is also envisioned that the configuration may be of a person, animal or plant as alive at one time, whether or not presently alive or presently older. Also, the configuration may be of an imaginary person, animal, plant or thing. Imaginary persons and animals may include include cartoon characters or characters from mythology.

The configuration may be merely an outline of silhouette, that is, the area within its periphery may be plain and flat. Preferably, some color is added to this area which would help enhance the artistic impression.

The pocket portion 2 may have a planar outwardly facing surface or, for enhanced effect, the pocket portion 2 may be configured into a three-dimensional shape which conforms to that of the creative artistic impression being represented by the outline.

An advantage of the identification band according to the invention is that the wearer may take some comfort in the appearance of the conveying means 10 and feel its contour. Providing a contour which can be felt is advantageous because it helps attract attention to the configuration, enhances the appeal of the outline of the contour and gives a child the ability to use his/her sense of touch while observing the configuration.

Also, when saved as a keepsake, the band may convey the impression that the hospital or medical facility is a warm, friendly, and caring place for children to stay because of the effort, even on small things like the identification wrist band, to make patients who are children more comfortable and at ease. Indeed, spreading good will in this manner provides an unexpected benefit from caring to make child patients feel more at ease, particularly when one considers that the parents may well show the identification band to friends and family, thereby spreading the word that the hospital or other medical facility is suited for children. Such unsolicited promotions through word of mouth is of great commercial value to the hospital or medical facility.

FIGS. 4-5 depict further embodiments for which two identical or complementary artistic configurations are provided each at a respective side of the pocket portion 2. The identification information 8 is to be visible through the area between the two configurations. The configurations may be transparent.

FIG. 3 shows two configurations of filled Easter baskets, which are associated with a holiday or special occasion. Other embodiments include two configurations of hot air balloons, apples, clouds, planets, stars, rainbows, halloween pumpkins, Christmas evergreen trees, Valentine hearts, Thanksgiving turkeys, Fourth of July fireworks, Birthday balloons, Holiday flowers, and joined hearts. The previously mentioned list of some configurations associated with various holidays special occasions and should not be construed as an exhaustive list. Another configuration is two joined hearts which are not spaced apart. All of these configurations are in a sense imaginary and constitute creative decorations or cartoon characters. Each configuration defines its own outline and may take three-dimensional form.

For ease in manufacture, the side of the configurations which face each other may be printed on the pocket portion 2; however, at least a portion of the opposite side and/or the top and bottom of each configuration should define an outline which may be felt. A person should be able to run their finger along the periphery and feel its contour and, if the face is three-dimensional, across its face to feel the shape. In addition, the two configurations need not be identical or complementary; they may differ from each other in appearance. Additional configurations may also be provided to define other portions of the periphery of the pocket portion.

FIG. 4 shows two configurations in the form of hearts which appear, when viewed from the front, to extend beyond or further define the adjoining periphery of the pocket portion. FIG. 5 shows two configurations resembling rocket ships which also appear to further define the periphery of the pocket portion. A snap-like fastener 12 is shown in which a peg element extends from the pocket portion through a hole in the strap portion 4. Another configuration includes two rabbits in three dimensional form which appear, when viewed from the front, to further define or extend beyond the adjoining periphery of the pocket portion.

FIGS. 2 and 3 exemplify embodiments in three dimensions which advantageously may include a colored layer for enhanced visual effect. Such a colored layer is made from the same material as the rest of the band but contains a color pigment and may be comprised of a colored or multi-colored plastic layer. Any of the embodiments of FIGS. 2 and 3 may be made into three dimensional form and comprise one or more colored layers. The colored layers may be tinted layers so as to allow a person to look through them.

For the sake of brevity, the drawings generally depict only the periphery of the pocket portion and the strap portion; a more detailed representation of the band element construction is depicted in U.S. Pat. No. 3,467,246 and so need not be repeated here. It is envisioned that the teaching of the present invention may be applied to any type of identification band of the prior art which has a pocket portion so long as its periphery may be changed or a configuration added to provide a creative artistic impression in accordance with the present invention.

As concerns "pocket portion", it is envisioned that such portion be capable of holding identification information between layers making up the pocket, with at least one face being transparent to allow viewing of the identification information from outside. Thus, the pocket portion may be of a type in which a slit is provided to allow for the insertion of identification information (in printed form on paper) or be of a type which laminates or otherwise seals (e.g., by heat) the information onto the inside facing side of the transparent face so that the information may be read from the outside looking through the transparent face.

Further, any of the configurations may be on the strap portion, rather than on the pocket portion. However, care must be taken to avoid having the configuration interfere with the fastening of the strap portion, whose fastening location may vary depending upon the size of the wrist of the wearer. Of course, the configuration may extend onto both the pocket and strap portions.

While the foregoing description and drawings represent the preferred embodiments of the present invention, it will be understood that various changes and modifications may be made without departing from the spirit and scope of the present invention.

What is claimed is:

1. An identification band, comprising:

an elongated band element having a pocket portion and a strap portion, the pocket portion being adapted to retain identification information pertaining to a wearer of the band, the pocket portion having a face through which may be viewed the identification information, the strap portion extending from one side of the pocket portion, the strap portion being adapted to be wrapped around the wrist of the wearer, the band element having a peripheral edge;

means for fastening the strap portion to an opposite side of the pocket portion; and means for conveying a creative aristic impression, said conveying means including a configuration resembling at least a portion of any one of a cartoon character, functional manufactured article, decoration associated with any one of a special occasion and holiday, natural object, person, plant and animal, said configuration having a peripheral edge which may be touched and which is configured to appear as at least a portion of an outline of that which is being resembled, said configuration extending outwardly from the band element at least as far as the peripheral edge of an adjacent portion of the band element, said peripheral edge of said configuration defining a portion of said band element.

2. The band as in claim 1, wherein the band element has an outermost planar face adjacent the configuration when viewed wrapped around the wrist of the wearer, the configuration having a three-dimensional form so as to extend outwardly out of the plane of the outermost planar face.

3. The band as in claim 1, further comprising the identification information of the wearer being enclosed in the pocket portion, the identification information being of a personal and medical nature.

4. The band as in claim 1, wherein the pocket portion has opposite sides, one of the sides having a periphery defined by the configuration, the other of the sides having a periphery defined by a further configuration.

5. The band as in claim 1, wherein the configuration is colored.

6. The band as in claim 1, wherein the configuration, the pocket portion and the strap portion are each composed of a common material which is of the same composition.

7. The band as in claim 1, wherein the peripheral edge of the configuration extends beyond the adjacent portion of the peripheral edge of the band element.

8. The band as in claim 1, wherein the band element has two peripheral edges which extend in the direction of elongation of the band element, a portion of the peripheral edge of the configuration extending outwardly beyond the two peripheral edges of the band element.

* * * * *